United States Patent [19]
Selim et al.

[11] Patent Number: 6,056,966
[45] Date of Patent: May 2, 2000

[54] METHOD AND COMPOSITIONS FOR TREATING IMPOTENCE

[75] Inventors: Sami Selim, Irvine; Robert Testman, Corona, both of Calif.; Ho-Leung Fung, Getzville, N.Y.; John A. Bauer, Westerville, Ohio

[73] Assignee: Baker Norton Pharmaceuticals, Inc., Miami, Fla.

[21] Appl. No.: 09/081,108

[22] Filed: May 18, 1998

[51] Int. Cl.[7] .............. A61K 6/00; A61F 13/00; A01N 13/02; A01N 13/24

[52] U.S. Cl. .......... 424/401; 424/449; 424/443; 514/645; 514/659; 514/663; 514/968; 514/969

[58] Field of Search .................... 514/659, 663, 514/645, 968, 969, 401; 424/481, 45, 449, 443, 434, 422

[56] References Cited

U.S. PATENT DOCUMENTS

| | | |
|---|---|---|
| 4,112,115 | 9/1978 | Coghlan . |
| 5,049,694 | 9/1991 | Bron et al. . |
| 5,059,603 | 10/1991 | Rubin . |
| 5,278,192 | 1/1994 | Fung et al. . |
| 5,489,610 | 2/1996 | Fung et al. . |
| 5,646,181 | 7/1997 | Fung et al. . |
| 5,820,587 | 10/1998 | Place ........................................ 604/54 |

FOREIGN PATENT DOCUMENTS

| | | |
|---|---|---|
| 0 359 335 | 3/1990 | European Pat. Off. . |
| 2200633 | 8/1990 | Japan . |
| WO 94/21248 | 9/1994 | WIPO . |
| WO 96/34583 | 7/1996 | WIPO . |
| WO 96/28142 | 9/1996 | WIPO . |
| WO 98/58633 | 12/1998 | WIPO . |

OTHER PUBLICATIONS

Chemical Abstracts 71:79612 (1969).
Truss et al., *Urology*, vol. 44, pp.553–556 (1994).
Wang et al., *J. Urology*, vol. 151, pp. 234–237 (1994).
Hellstrom et al., *J. Urology*, vol. 151, pp. 1723–1727 (1994).
Anderson, *Annals Pharm.*, vol. 27, pp. 1203–1205 (1993).
Nunez et al., *J. Urology*, vol. 150, pp. 1241–1243 (1993).
Lerner et al., *J. Urology*, vol. 149, pp. 1246–1255 (1993).
Chen et al., *J. Urology*, vol. 147, pp. 1124–1128 (1992).
Rajfer et al., *New England J. Med.*, vol. 326, pp. 90–94 (1992).
Steif et al., *J. Urology*, vol. 148, pp. 1437–1440 (1992).
Knispel et al., *Urol. Res.*, vol. 20, pp. 253–257 (1992).
*The Lancet*, vol. 340, pp. 882–883 (1992).
Talley et al., *Annals of Int. Med.*, vol. 103, p. 804 (1985).

*Primary Examiner*—Thurman K. Page
*Assistant Examiner*—Todd D Ware
*Attorney, Agent, or Firm*—Simona A. Levi-Minzi

[57] ABSTRACT

Pharmaceutical compositions in topical or parenteral form containing specific organic mono- or dinitrates, some of them novel compounds, are effective in treating male impotence and erectile dysfunction through topical or intracavernosal administration to the penis. Methods of treatment utilizing the mono- or dinitrate-containing compositions are also disclosed.

29 Claims, 13 Drawing Sheets

METHOD AND COMPOSITIONS FOR TREATING IMPOTENCE

REFERENCE TO DISCLOSURE DOCUMENT

This application incorporates material included in Disclosure Document No. 401878, filed in the Patent and Trademark Office on Jul. 1, 1996.

BACKGROUND OF THE INVENTION

1. Field of the Invention

This invention relates to methods and compositions for treating male impotence and erectile dysfunction.

2. Description of the Prior Art

The process of erection is generally a selective vasodilation of the spongy penile tissue and corpus cavemosum and reductions in outflow, leading to blood pooling, elevation of intra-cavernous pressure, and therefore erection.

Conventional pharmaceutical therapies for impotence or erectile dysfunction primarily include local administration of vascular smooth muscle relaxants, for example papaverine or prostaglandin E1, or α-adrenoceptor antagonists, such a phentolamine, resulting in penile erection because of an increase in arterial inflow of blood, distension of sinusoids and possible restriction of venous outflow. Thus, intracavernous injection of vasoactive drugs offers impotent patients a form of therapeutic management, and allows one of the tests for differential diagnosis between vasculogenic and other etiologic forms of impotence. Papaverine and prostaglandin E1 are also used in the assessment of pharmacological response of penile erectile tissues under experimental conditions (see Chen et al., *J. Urol.*, 147:1124–1128, 1992).

Other pharmaceutical treatments for impotence have been practiced in the prior art. These include systemic administration of male hormonal preparations such as methyltestosterone and testosterone esters, as well as administration of various naturally occurring plant extracts believed to have aphrodisiac properties, such as yohimbine, ginseng, strychnine and the like. Non-pharmacological therapeutic modalities for impotence include the surgical implantation of penile prostheses and the use of tourniquetlike devices which fit tightly around the shaft of the penis and restrict the flow of blood through the surface veins and the deeper dorsal vein to prolong erection.

All of the foregoing prior art treatment methods suffer from obvious and serious disadvantages. The injection of papaverine and other vasoactive drugs meets with variable success and variable duration of response, and repeated injections into the penis can be painful and traumatic. In some patients these agents cause priapism (undesirable sustained erection), which can lead to structural damage to the organ. The administration of methyltestosterone or testosterone esters may cause toxic effects or inhibit endogenous testosterone formation and spermatogenesis. Orally administered aphrodisiac substances are of marginal and erratic efficacy, and some have significant adverse side effects. The use of surgical implants or tourniquet-like devices can lead to serious problems of infection and trauma, and cause discomfort to both male and female partners.

Several recent studies have shown the obligatory role of nitric oxide for the erection process (see for example Rajfer et al., *N. Eng. J. Med.*, 326:90–94, 1992). Rajfer has concluded that stimulation of the local nerve leads to the production of NO, which increases blood flow in the penile arteries and relaxes the cavernous spaces. When these cavernous spaces are filled they compress venous egress from the corpus cavernosum, leading to an erectile response. Administration of exogenous NO donors may therefore be useful for promoting erections. Several patents have issued regarding the use of nitroglycerin (NTG) and linsidomine applied topically or via intracavernosal injection to treat impotence and erectile dysfunction.

It has been well established that NTG causes relaxation of penile smooth muscle and vascular tissue, including cavernosal tissue. Studies using ointment formulations have demonstrated vasodilation and subsequent engorgement. There is however less convincing evidence that NTG given as 2–10% ointment or plaster applied topically would result in an erection sufficient for vaginal penetration. Using 2% NTG ointment, 18/26 patients had increase in circumference and 7/20 patients had a 50% increase in tumescence (Owen et al. J. Urol. 141:546, 1989).

Studies by Cavallini (J. Urol. 146:50, 1991) showed that, using a single blind design, in 51 patients there was an elevation in penile circumference and rigidity with 10% NTG ointment. In other nonblinded studies, NTG plasters applied locally for several hours, resulted in relatively poor responses in 90% of the patients in the laboratory and 60% of patients at home (Meyoff et al. Br. J. Urol. 69:88 1992). In another study, 30% of patients achieved erections sufficient for vaginal penetration at home whereas 71% of patients had some response (Sonksen, Biering-Sorensen, Paraplegia 30:554, 1992). Using NTG patches in a double blind study, the response to active drug was about 81%, whereas it was 19% with placebo (Claes and Baert, Urol. Int. 44:309; 1989). This was based on post test interviews and not patient diaries or questionnaires which would have been more accurate.

Sexual response was tested in only 3 of 5 studies published studies evaluating erectile response to nitrates. Statistical methods were not evaluated in most of the studies and only one trial reported that NTG had a response that was better than papaverine, another vasodilator, or placebo. In many of these trials headaches were a common occurrence and it is unclear what NTG dose is needed or its duration of action. Furthermore, it was shown that many patients will not demonstrate a useful response to NTG. This may occur because of ultrastructural injury to the smooth muscle, failure of veno-occlusion, or direct venodilation on subtunical veins. Other factors that limit the therapeutic potential of NTG include decrease in systemic blood pressure and development of headache.

It has been disclosed in PCT Application Publication WO 96/34583 that certain organic nitrites, particularly dinitrites such as 1,5-pentane dinitrite, are effective in inducing erection even when applied topically to the penis, and are almost devoid of undesirable side effects caused by systemic vasodilation. However, the nitrites have been found to be irritating to dermal tissues and may, therefore, not be suitable for widespread therapeutic use.

Improved pharmaceutical compositions and methods are required for treating impotence while avoiding the adverse effects experienced with prior art treatment modalities.

SUMMARY OF THE INVENTION

The present invention resides, briefly stated, in the local (topical or intracavernosal) administration of certain organic mono- and dinitrates to the penis to induce and maintain erection with selective local (cavernosal) vasodilation and little or no "downstream" systemic vasodilating effects. The invention also comprehends mono- and dinitrate-containing topical and parenteral pharmaceutical compositions for treatment of impotence.

DETAILED DESCRIPTION OF THE INVENTION

Figure 1:
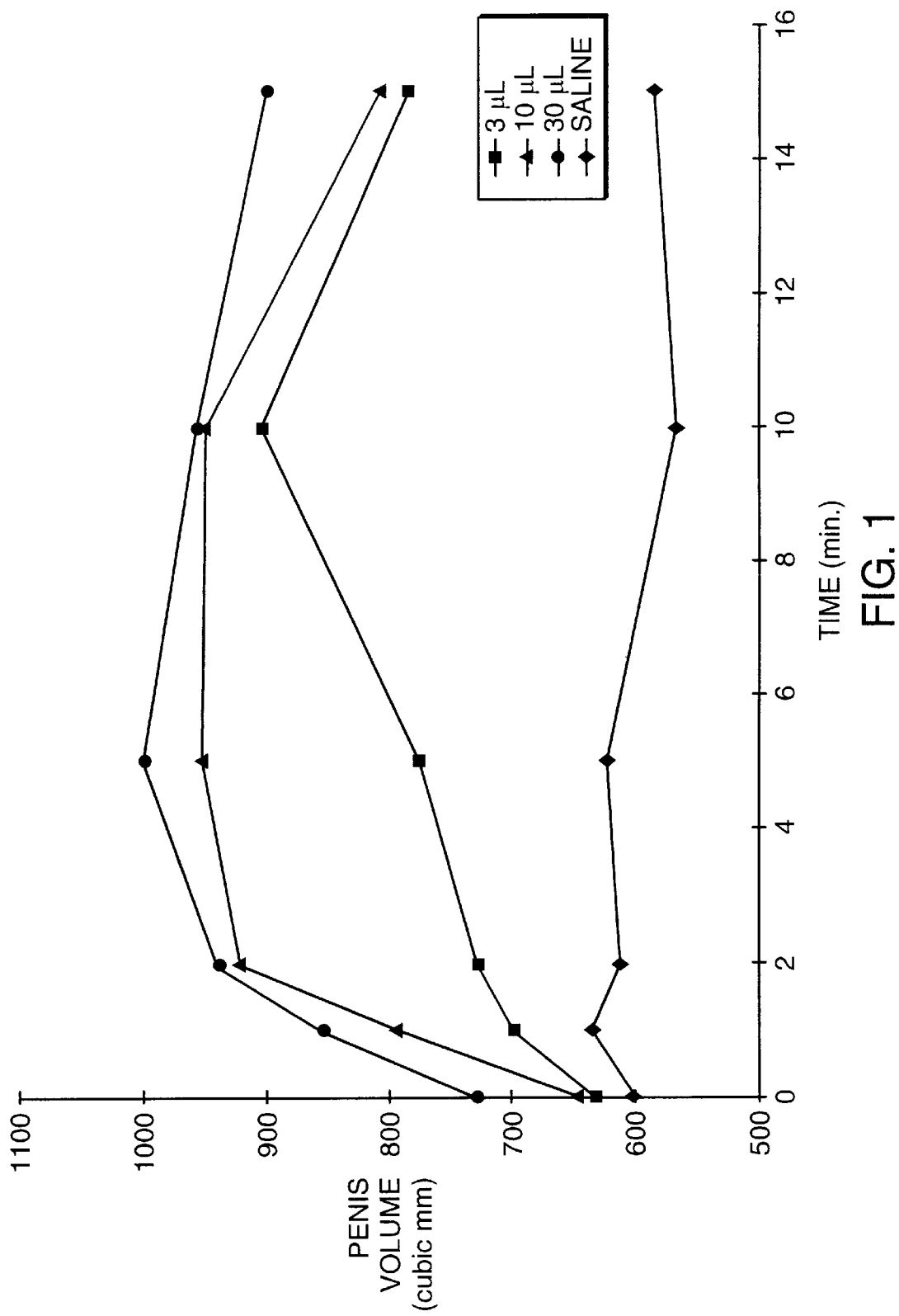
FIG. 1 is a graph illustrating the dose-related changes in penile volume over time caused by topical application of 1,5-pentane dinitrate (1,5-PDN) to the guinea pig penis.

The present invention pertains to the local administration of certain vasodilating organic mono- and dinitrates to the penis, either by application of nitrate-containing topical pharmaceutical compositions (e.g., ointments, creams, gels, lotions, liquids, sprays and the like) or by intracavernosal injection of parenteral nitrate-containing compositions, for effective treatment of male impotence and erectile dysfunction in humans.

It has been discovered that the use of certain organic mono- and dinitrates never employed in the prior art to treat impotence and related conditions, and some of which are novel compounds, yield unexpected therapeutic advantages in comparison with vasodilating agents which were used for the same purposes in the art, including closely related vasodilators such as nitroglycerin (NTG). Chief among these unexpected advantages are an increase in the degree of tumescence achieved and a substantial decrease in systemic vasodilating effects, resulting in a much smaller drop in systemic blood pressure than occurs with NTG and other prior art nitrate vasodilators. The combination of these effects renders these organic mono- and dinitrates more effective and safer than other vasodilators previously used to induce or maintain erection. The subject organic nitrates also may be less prone to causation of adverse side effects such as the severe headaches that can be caused by nitroglycerin, because of reduced systemic action.

It is not known why topical application of the organic mono- and dinitrates of the invention causes a greater increase in penile volume than NTG. It is speculated that the differences in activity may be related to the more efficient generation of NO by the dinitrates in the corpus cavernosum, or to the different penetration kinetics of the two agents that does not allow significant peripheral vasodilation which can result in detumescence.

The mono- and dinitrate compounds used in the present invention have also been found to be less volatile, more stable chemically and less irritating upon topical application to the skin than the organic nitrites disclosed, e.g., in PCT application WO 96/34583.

Topical pharmaceutical compositions containing one or a mixture of the organic mono- and dinitrates for use in the present invention preferably contain at least one active nitrate ingredient in a concentration sufficient to supply from about 0.1–40 mg of active nitrate ingredient per dose (e.g., per application of about 50 to 800 mg of topical composition), in a pharmaceutically acceptable topical carrier or vehicle. Such vehicle can be in the form of an ointment, gel, cream, lotion, liquid, spray, or any other form known to those skilled in the pharmaceutical and formulation arts. The vehicles used in the topical compositions may contain any conventional solvents, emollients, humectants, surfactants, opacifying and coloring agents, penetration enhancers, and other additives commonly used in topical vehicles. The inactive ingredients in the topical compositions should be chemically compatible with the active nitrate ingredients and of low irritation potential so that the compositions can be safely applied to the sensitive areas of the penis.

Topical carriers useful for formulating mono- or dinitrate-containing compositions include, for example, ointment, gel and cream bases containing white petrolatum, paraffin wax, capryl ic/capric dig lyceryl succi nate, di isopropyl adipate and/or ethoxydiglycol.

Examples of topical carriers suitable for use with the organic nitrates of the present invention are set forth in U.S. Pat. No. 5,059,603, the disclosures of which are incorporated herein by reference.

The subject organic nitrates may also be incorporated into tapes and patches to be applied to the penis. These drug-releasing tapes and patches may be prepared in accordance with the technology widely utilized for slow-release transdermal vehicles containing cardiovascular (e.g., antianginal) drugs.

A number of different transdermal products which can employ the organic nitrates in accordance with the invention are described by Curtis Black, "Transdermal Drug Delivery", *U.S. Pharmacist*, November 1982, pp. 49–75, which disclosure is hereby incorporated by reference. Additionally, exemplary patents relating to delivery systems include U.S. Pat. Nos. 4,191,015; 3,742,951; 4,191,015; 3,742,951 and 4,262,003 which disclose using penetration enhancers to control delivery rates, which disclosures are hereby incorporated by reference.

Moreover, the topical nitrate-containing compositions, particularly in the form of ointments or gels, can be coated onto the inside of a condom, for example, a latex condom, which can be applied to the penis in conventional fashion. Such mode of administration serves the dual purposes of promoting erection and providing a contraceptive and disease-transmission barrier during intercourse. Alternatively, devices such as condoms and penis rings can be impregnated with the nitrate-containing compositions to achieve a comparable effect.

Parenteral vehicles for nitrate-containing compositions in accordance with the invention include solutions or dispersions of one or a mixture of organic mono- or dinitrates in a pharmaceutically acceptable parenteral carrier. Such carriers may include non-aqueous solvents or diluents, e.g., ethanol, benzyl alcohol or propylene glycol, and may also include as solvents, diluents or stabilizers, glycerine, povidone, lecithin, sorbitan monooleate or trioleate, polysorbate 80, peanut oil, castor oil, and other triglycerides. Lipid emulsion carriers may also be employed. The parenteral composition should have a sufficient concentration of active nitrate ingredient to provide about 0.01–1.0 mg of mono- or dinitrate per injectable dose, said dose being about 0.1 to 0.5 ml of parenteral composition.

Examples of organic nitrates which have been found useful in the method of the invention are shown in Table 1. Analytical purity by gas chromatography mass spectroscopy of each is also presented. Many of these organic nitrates are novel compounds, never previously synthesized, as far as revealed by extensive searching of the literature and computer databases.

TABLE 1

1,5-PENTANE DINITRATE ANALOGS SUMMARY

| Compound | Structure | Purity (%) |
|---|---|---|
| 2-Pentane nitrate | [structure] | 96.7 |
| 1,5-Pentane dinitrate | $O_2NO$–[chain]–$ONO_2$ | 99.5 |
| 1,4-Butane dinitrate | $O_2NO$–[chain]–$ONO_2$ | 99.6 |
| 1,6-Hexane dinitrate | $O_2NO$–[chain]–$ONO_2$ | 98.3 |
| 1,7-Heptane dinitrate | $O_2NO$–[chain]–$ONO_2$ | 96.2 |
| Isoamyl nitrate | [structure]–$ONO_2$ | 100.0 |

TABLE 1-continued 1,5-PENTANE DINITRATE ANALOGS SUMMARY

| Compound | Structure | Purity (%) |
|---|---|---|
| Isobutyl nitrate | [structure]–$ONO_2$ | 99.8 |
| Neopentyl nitrate | [structure]–$ONO_2$ | 100.0 |
| 2-Methyl-1-propene-3-nitrate | $O_2NO$–[structure] | 100.0 |
| 2-Methyl-2-butene-4-nitrate | $O_2NO$–[structure] | 100.0 |
| 1-Pentene-5-nitrate | $O_2NO$–[structure] | 93.3 |
| Cyclopentyl nitrate | [structure]–$ONO_2$ | 100.0 |
| 1,4-Cyclohexyl dinitrate | $O_2NO$–[structure]–$ONO_2$ | 97.6 |
| 1-Pentane nitrate | $O_2NO$–[chain]–$ONO_2$ | 99.5 |

The following examples are presented to further illustrate the compositions and methods of the present invention and the organic mono- and dinitrate compounds which may be effectively used, among others, in practicing the novel method. These examples should not be viewed, however, as providing compounds, compositions, formulations or methods of administration which must be practiced exclusively in order to come within the present invention.

EXAMPLE 1

Preparation of 1,5-Pentane Dinitrate

90% $HNO_3$ (30 ml) was added dropwise to a stirred solution of 1,5-pentane diol (10 g) in $H_2O$ (25 ml). The reaction mixture was cooled (0° C.), concentrated $H_2SO_4$ (20 ml) was added dropwise and the solution allowed to warm to room temperature slowly with constant stirring (3 hours). The top layer was decanted, dissolved in $CH_2Cl_2$ (70 ml), washed with $H_2O$ (75 ml) and saturated $NaHCO_3$ (3×75 ml), dried (anhy. $Na_2SO_4$) and concentrated in vacuo. The residue was then distilled under vacuum to afford the product (1,5-PDN) as a colorless liquid.

The remaining dinitrates and certain mononitrates useful in the practice of the invention can be prepared by syntheses analogous to that set forth above for 1,5-PDN. Thus, for example, 1,4-butane dinitrite may be prepared using an aqueous solution of 1,4-butane diol, and so forth. Mononitrates which could not be synthesized using the method in Example 1 were synthesized as shown in Example 2.

EXAMPLE 2

Preparation of 2-Methyl-1-Propene-3-Nitrate 7.41 grams of silver nitrate was weighed into a 100 mL round bottom flask. Eight mL of acetonitrile was added and the solution was stirred until the silver nitrate dissolved. To the silver nitrate solution was added 4 mL of 3-bromo-2-methylpropene in 21 mL acetonitrile. A yellow precipitate is formed immediately upon addition. The reaction mixture was stirred for 30 minutes after addition, then filtered. Thirty mL of water was added to the filtrate, and then the mixture was extracted with three 30 mL portions of hexane. The hexane layers were combined and dried over sodium sulfate. The solvent was removed under reduced pressure and the crude reaction material purified by fractional distillation to yield 0.9 mL of final product, 2-methyl-1-propene-3-nitrate.

EXAMPLE 3

Topical Application of Nitrates in Guinea Pigs

Test Procedure

Sixteen (16) male outbred Hartley guinea pigs were weighed and placed into treatment groups as follows:

| N | Treatment Agent | Dose |
| --- | --- | --- |
| 4 | 1,5-pentane dinitrate | 3 µL |
| 4 | 1,5-pentane dinitrate | 10 µL |
| 4 | 1,5-pentane dinitrate | 50 µL |
| 4 | normal saline | 30 µL |

The animals were placed in dorsal recumbency and held in place by restraints. The penis was extruded from the prepuce. Care was taken to not manipulate the penis. Length and diameter measurements were made using digital calipers. The length measurement was taken from the prepuce to the tip of the glans when the penis was extended. The diameter was taken 0.5 cm proximally from the tip of the glans.

The appropriate amount of test material was applied with a Wiretrol™ pipette to the base of the exposed penis. When application was complete, a timer was started. Measurements were taken at 0, 1, 2, 5, 10 and 15 minutes after application or until detumescence was observed.

Results

Data collected during this study are graphically represented in FIG. 1. Inspection of the data indicates that the 1,5-pentane dinitrate was significantly more effective than the saline control in increasing penile volume, and that a dose-related response was observed with 1,5-PDN.

The same procedure was followed to topically apply a series of various other nitrate and dinitrate compounds (in neat form) to the penis of guinea pigs. A summary of the activity of this series of nitrate compounds is shown in Table 2, with the AUC and peak effect values for each compound compared to 1,5-PDN.

TABLE 2

| Compound | AUC | % of 1,5-PDN | Peak Effect (% change) | % of 1,5-PDN | Time of Peak Effect (min) |
| --- | --- | --- | --- | --- | --- |
| 1,5-Pentane-dinitrate | 442 | 100 | 38.7 | 100 | 5 |
| 1,4-Butane-dinitrate | 403 | 91 | 35.5 | 92 | 2 |
| 1,6-Hexane-dinitrate | 349 | 79 | 31.8 | 82 | 5 |
| 1,7-Heptane-dinitrate | 460 | 104 | 39.3 | 102 | 5 |
| Isoamyl nitrate | 309 | 70 | 40.3 | 104 | 2 |
| Neopentyl nitrate | 376 | 85 | 45.2 | 117 | 2 |
| Isobutyl | 367 | 83 | 38.1 | 98 | 2 |
| Cyclopentyl nitrate | 380 | 86 | 31.8 | 82 | 10 |
| 2-Pentane nitrate | 323 | 73 | 36.0 | 93 | 5 |
| 1-Pentene-5-nitrate | 309 | 70 | 35.4 | 91 | 2 |
| 2-Methyl-2-butene-4-nitrate | 305 | 69 | 32.6 | 84 | 5 |
| 1,4-Cyclohexyl dinitrate | 225 | 51 | 27.9 | 72 | 2 |
| 1-Pentane nitrate | 234 | 53 | 25.9 | 67 | 2 |
| 1-Methyl-1-propene-3-nitrate | 265 | 60 | 28.6 | 74 | 5 |

All of the compounds listed above had AUC values no less than 50% of the AUC of 1,5-PDN. Organic nitrate compounds having topical activity AUC values in this animal model equal to at least about 50% of the AUC value of 1,5-PDN can be considered potent stimulators of erection and can be used in the present invention.

EXAMPLE 4

Topical Application of Nitroglycerin in Guinea Pigs

Test Procedure

The same test procedure was followed as in Example 3, but applying a 10% solution of NTG to the penis in varying dosage amounts.

Twelve (12) male Hartley guinea pigs were placed into treatment groups as follows:

| N | Treatment Agent | Dose |
| --- | --- | --- |
| 4 | 10% Nitroglycerin Solution | 3 µL |
| 4 | 10% Nitroglycerin Solution | 10 µL |
| 4 | 10% Nitroglycerin Solution | 30 µL |

Results

Figure 2:
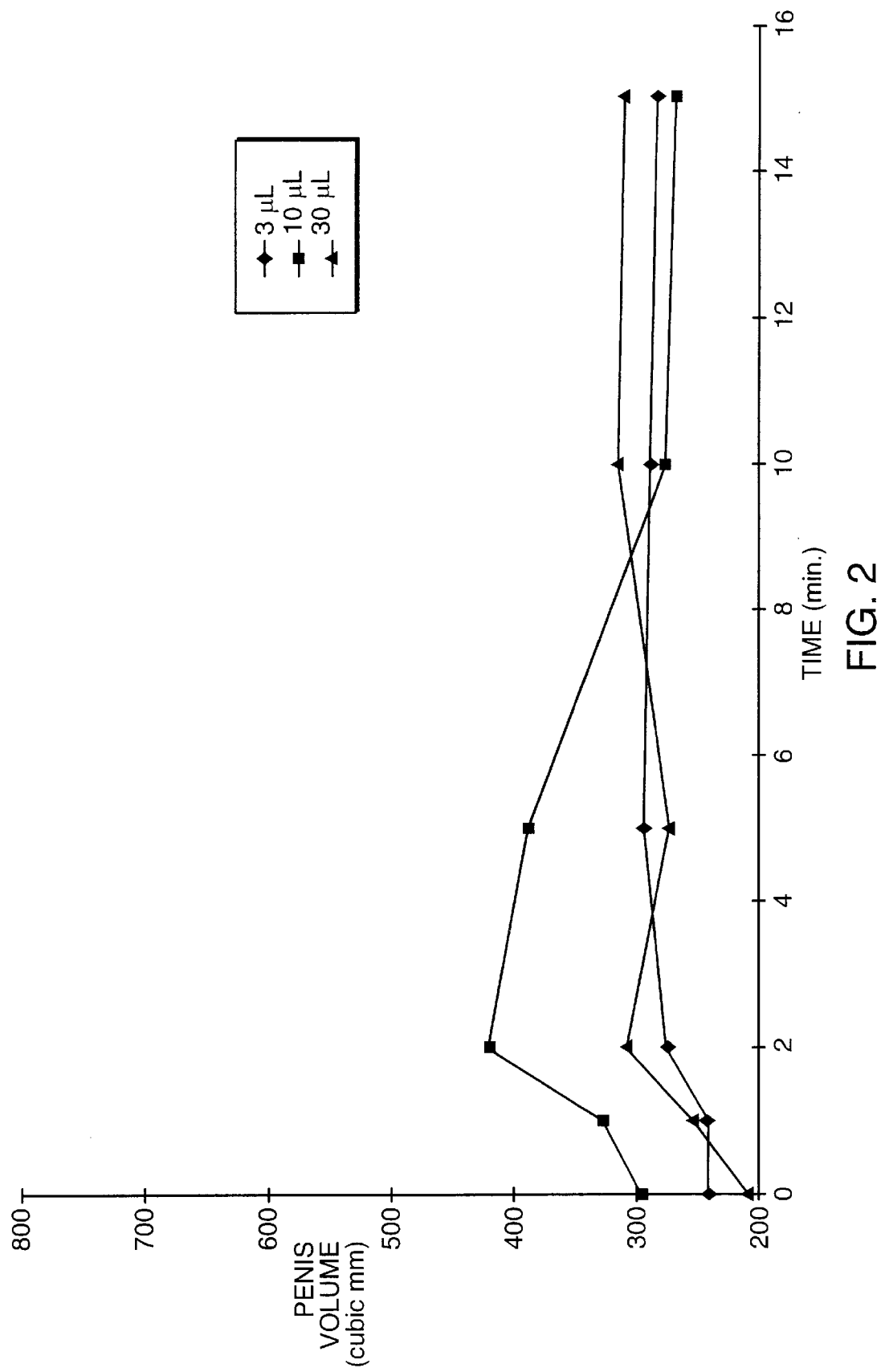
FIG. 2 is a graph illustrating the dose-related changes in penile volume over time caused by topical application of a 10% nitroglycerin (NTG) solution to the guinea pig penis.
Figure 3:
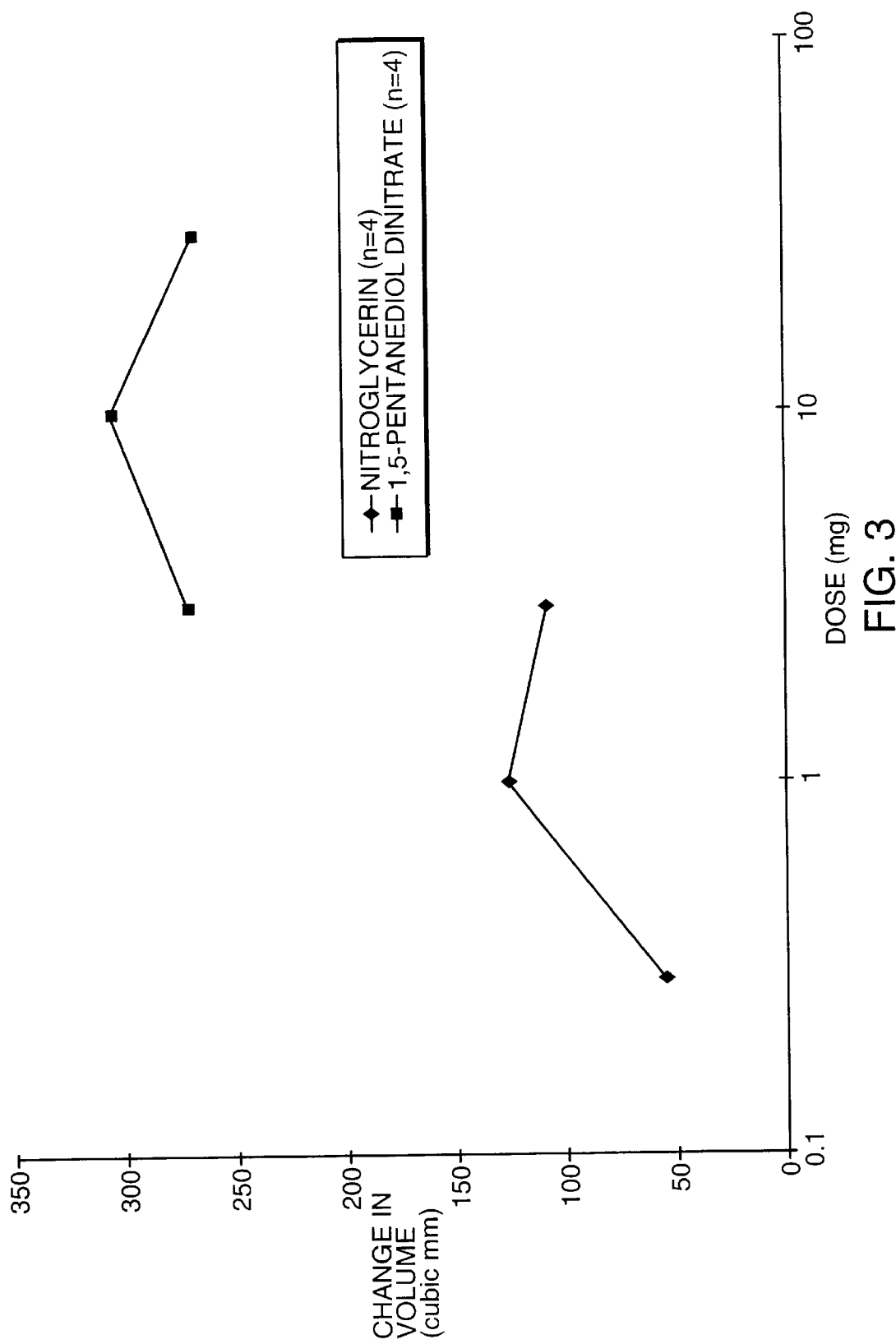
FIG. 3 is a graph illustrating the peak increases in penile volume caused by topical application of NTG and 1,5-PDN, respectively, to the guinea pig penis.
Figure 4:
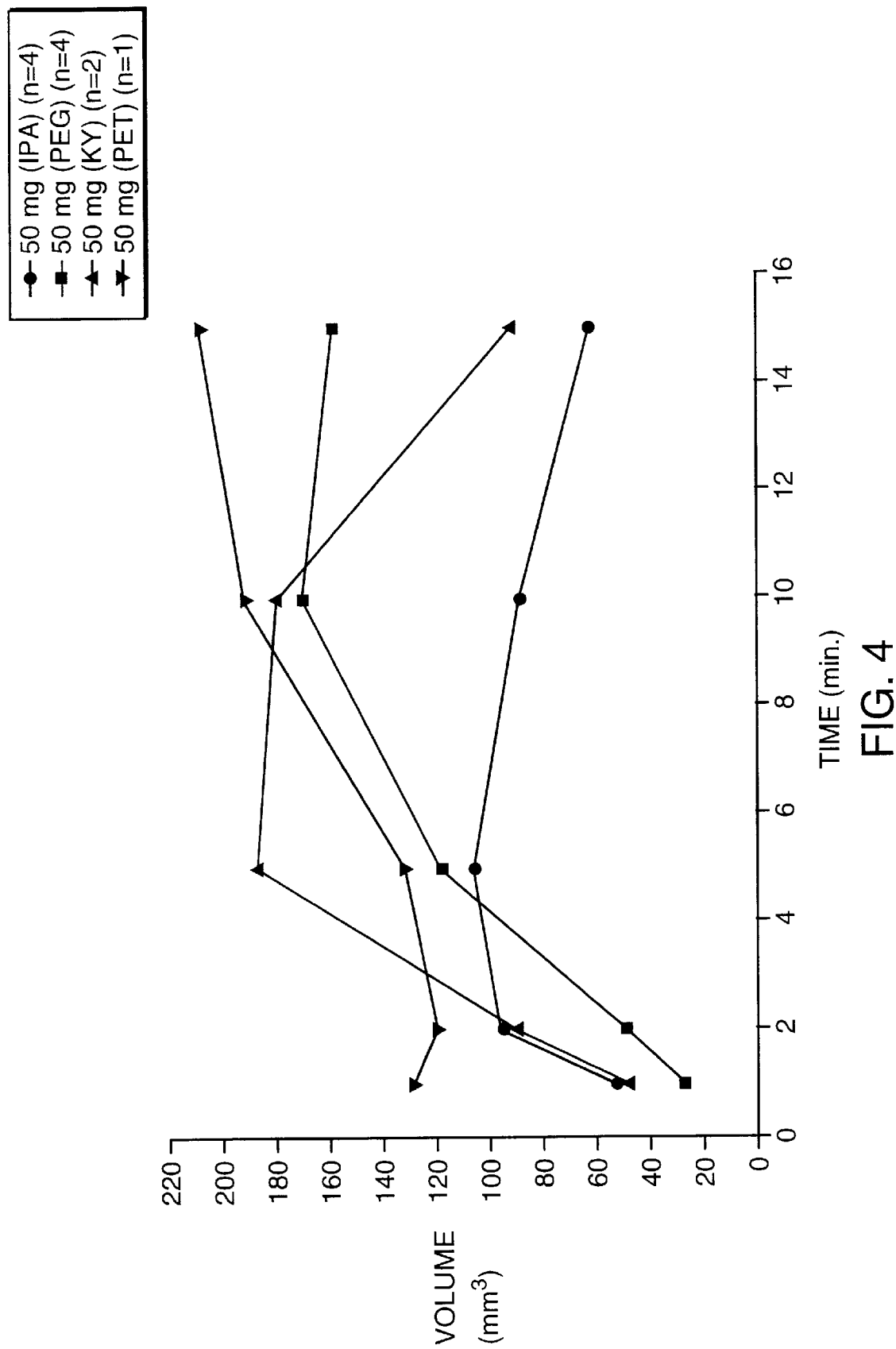
FIG. 4 is a graph illustrating the changes in volume of the penis in guinea pigs over time after application of 5% 1,5-PDN (about 2.5 mg in 50 mg of topical product) prepared in various formulations: 1) isopropyl alcohol, 2) propylene glycol, 3) KY jelly and 4) petrolatum.
Figure 5:
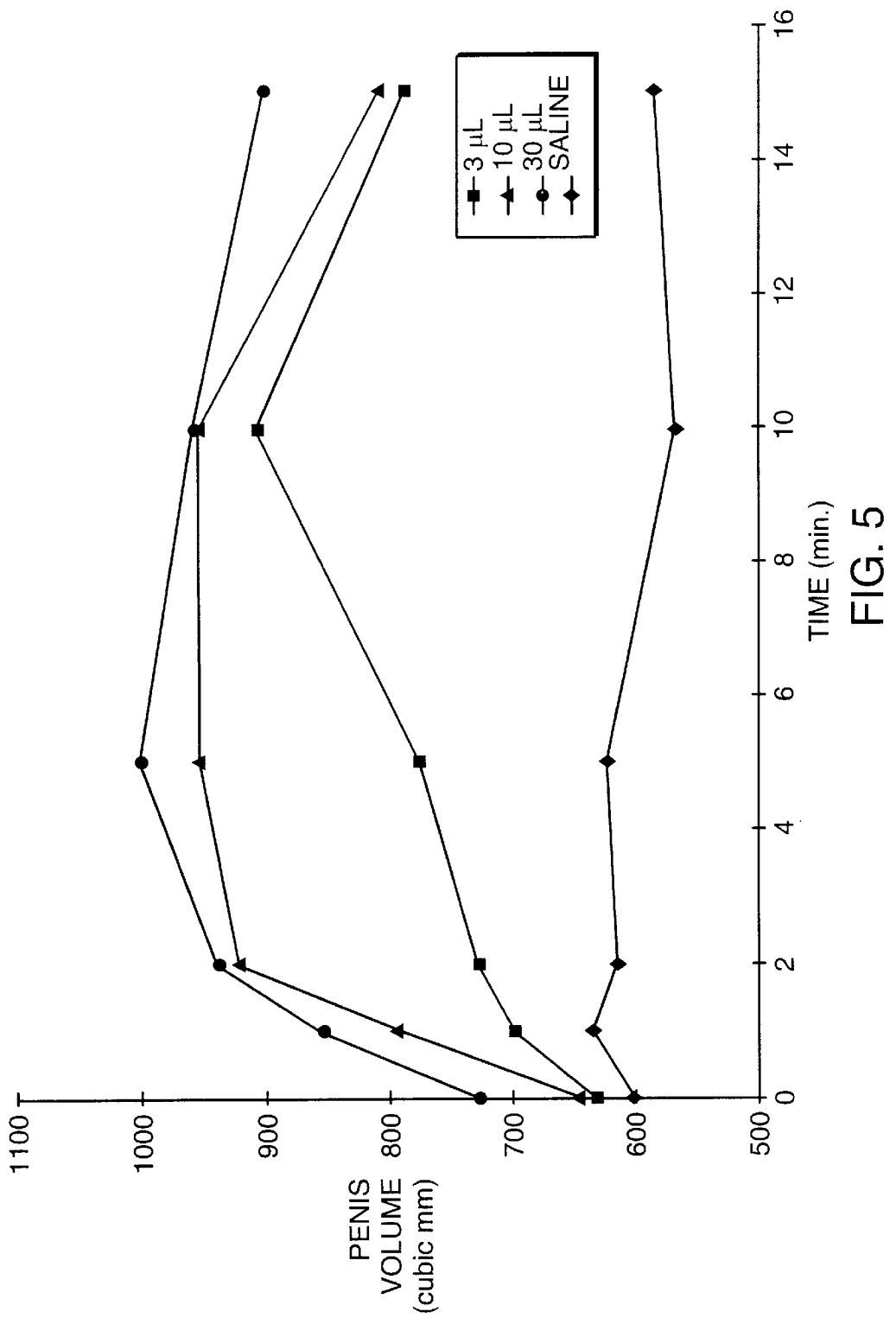
FIG. 5 is a graph illustrating the dose-related changes in penile volume over time caused by topical application of 1,5-pentane dinitrite to the guinea pig penis.

The data collected during this study are graphically represented in FIG. 2. The data indicate that NTG had a minimal effect on penis volume as compared to 1,5-PDN. This difference is illustrated in FIG. 3 which shows the larger effect of 1,5-PDN in producing erection, as reflected by peak penis volume changes.

EXAMPLE 5

Intracavernosal Injection of Dinitrates in Rats

Description of Rat Model

Rats are anesthetized with a long-acting barbiturate (Inactin), and a catheter is inserted in the left femoral artery for the measurement of systemic blood pressure. The penile area is exposed and a needle is inserted in the corpus cavernosal area (the right crus) for the measurement of intracavernosal pressure, and for intracavernosal injection of drugs.

The determination of rat "erection" is through the measurement of cavernosal pressure. In humans and animals the pressure is initially very low (approx. 5–10 mmHg), and during erection it rises to 60–90% of systemic blood pressure (depending on the species and needle placement).

Test Procedure

Three groups of laboratory rats (n=4–7 in each group) were catheterized as described above and baseline cavernosal and arterial blood pressure values were determined. The test animals received intracavernosal injections of NTG or other organic NO donors in ethanol solution in varying molar concentrations. The three groups received, respectively, NTG (group 1); 1,5-pentane dinitrate or ethanol placebo (group 2); and sodium nitroprusside or ethanol placebo (Group 3).

The maximum changes in cavernosal and arterial blood pressure were determined for each animal.

Results

Figure 6:
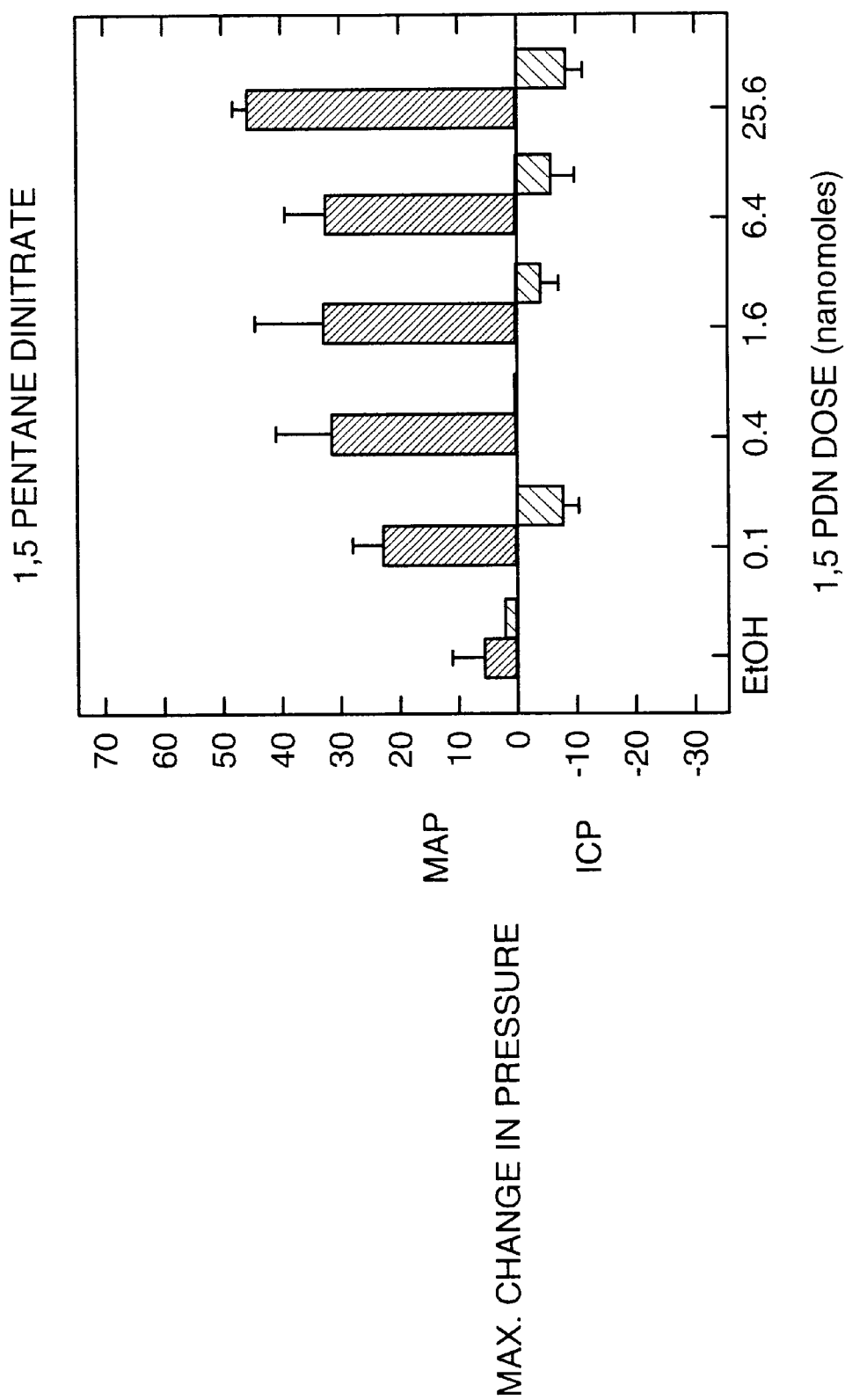
FIG. 6 is bar graph illustrating the maximum changes in mean arterial blood pressure and cavernosal pressure in anesthetized rats administered varying dosage amounts of 1,5-PDN by intracavernosal injection.
Figure 7:
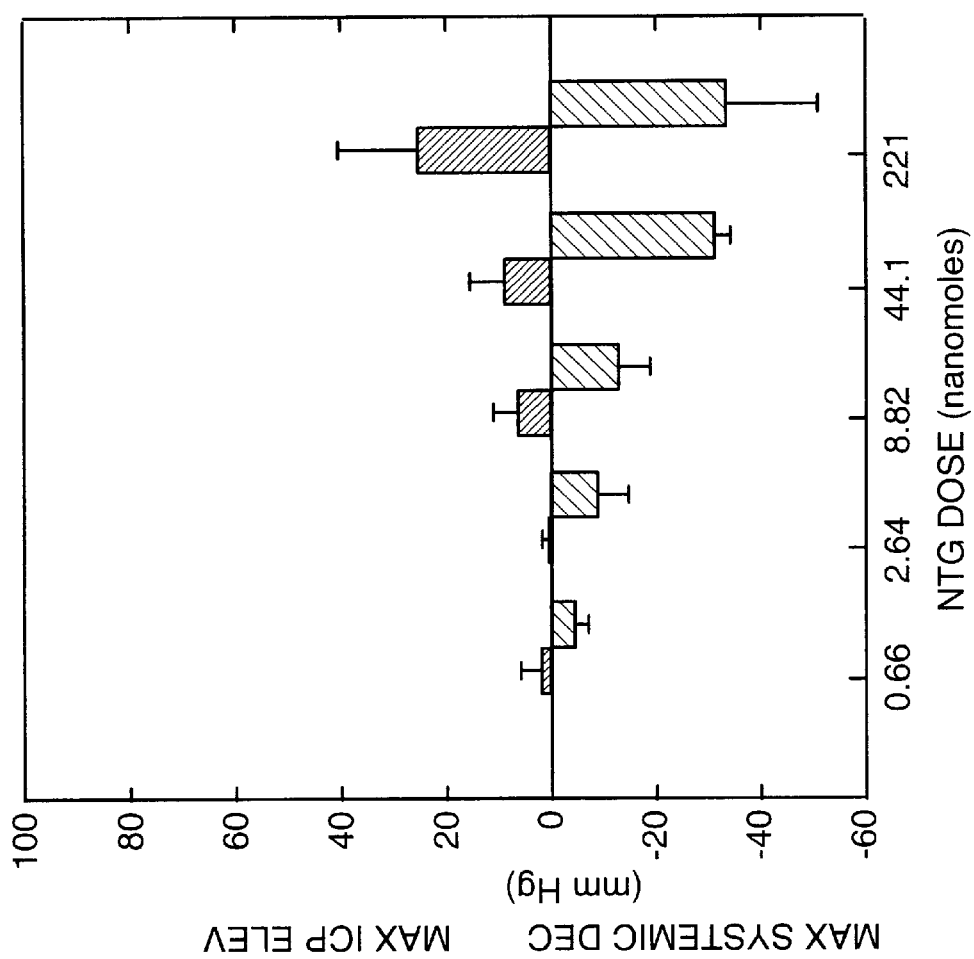
FIG. 7 is bar graph illustrating the maximum changes in mean arterial blood 5 pressure and cavernosal pressure in anesthetized rats administered varying dosage amounts of NTG by intracavernosal injection.
Figure 8:
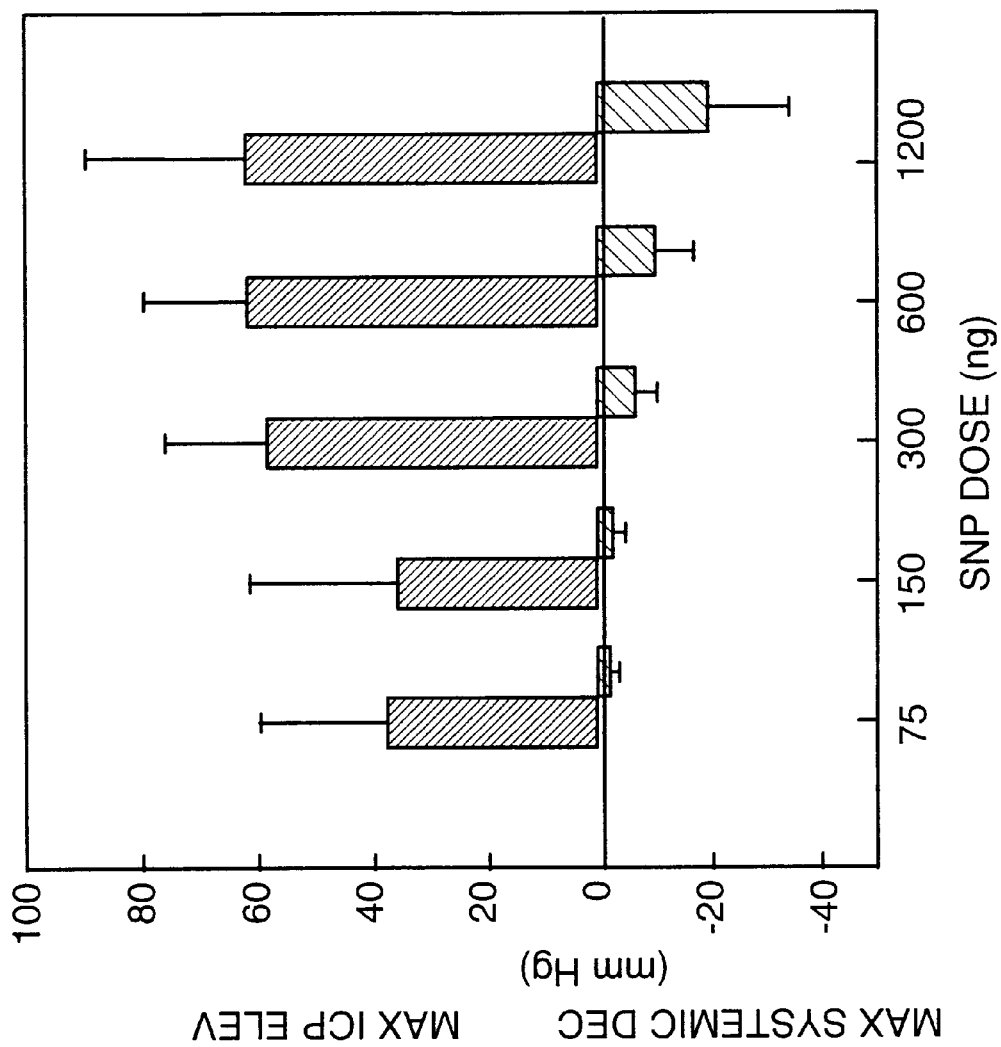
FIG. 8 is bar graph illustrating the maximum changes in mean arterial blood pressure and cavernosal pressure in anesthetized rats administered varying dosage amounts of sodium nitroprusside (SNP) by intracavernosal injection.

The mean changes in cavernosal and arterial blood pressure of the four test groups are reflected in FIGS. 6–8 respectively. As reflected in FIG. 7, injection of nitroglycerin caused relatively small, dose-dependent increases in intracavernosal pressure, and simultaneously caused almost equivalent systemic ("downstream") reductions in arterial blood pressure (i.e., over 30 mmHg at the highest dose used).

By contrast, as reflected in FIGS. 6–8, injection of either an organic dinitrate or sodium nitroprusside caused greater changes in mean intracavemosal pressure in the test animals while having little or no effects on systemic blood pressure. However, sodium nitroprusside does not penetrate the skin rapidly and can produce toxic cyanide metabolites. Thus, sodium nitroprusside cannot be used as a transcutaneous drug for penile dysfunction.

EXAMPLE 6

Intravenous Injection of NTG vs. 1.5-Pentane Dinitrate in Rats

Test Procedure

Rats (n=3) with indwelling catheters in the femoral artery for blood pressure measurements and vein for drug administration were given 1 dose of NTG (30 µg) and 6 doses of 1,5-PDN (30 µg–2000 µg) or vehicle (ethanol) in the conscious state. Changes in mean arterial blood pressure (diastolic blood pressure+⅓ (systolic–diastolic blood pressure)) were assessed after each dose of nitrate was given. About 0.5 hr to 1 hr separated the administration of each drug and dose.

Results

Figure 9:
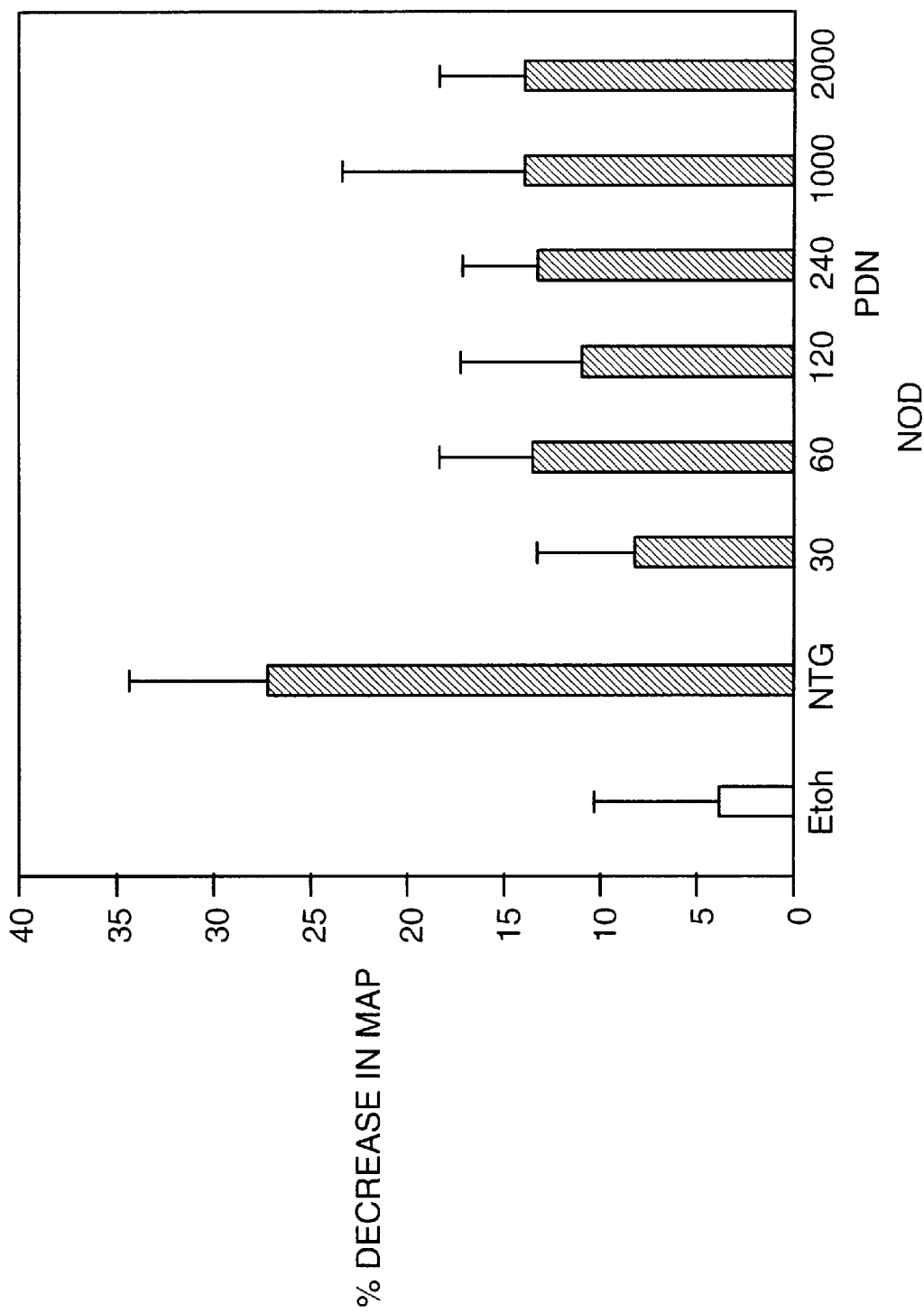
FIG. 9 is a bar graph illustrating the maximum changes in mean arterial blood pressure in conscious rats administered intravenous NTG (30 µg) and 1,5-PDN (30 to 2000 µg). Ethanol (EtOH) was used to solubilize the nitrate compounds and its effect on blood pressure are shown.

The mean changes in mean arterial pressure of NTG and 1,5-PDN are shown in FIG. 9. NTG resulted in about a 25% decrease in arterial pressure whereas the same dose of 1,5-PDN caused only about an 8% reduction in blood pressure. Higher doses of 1,5-PDN resulted in average decrease of 12–14% in blood pressure. These findings are surprising given the similarity in vascular relaxation between the two drugs.

EXAMPLE 7

Vascular Reactivity

Figure 10:
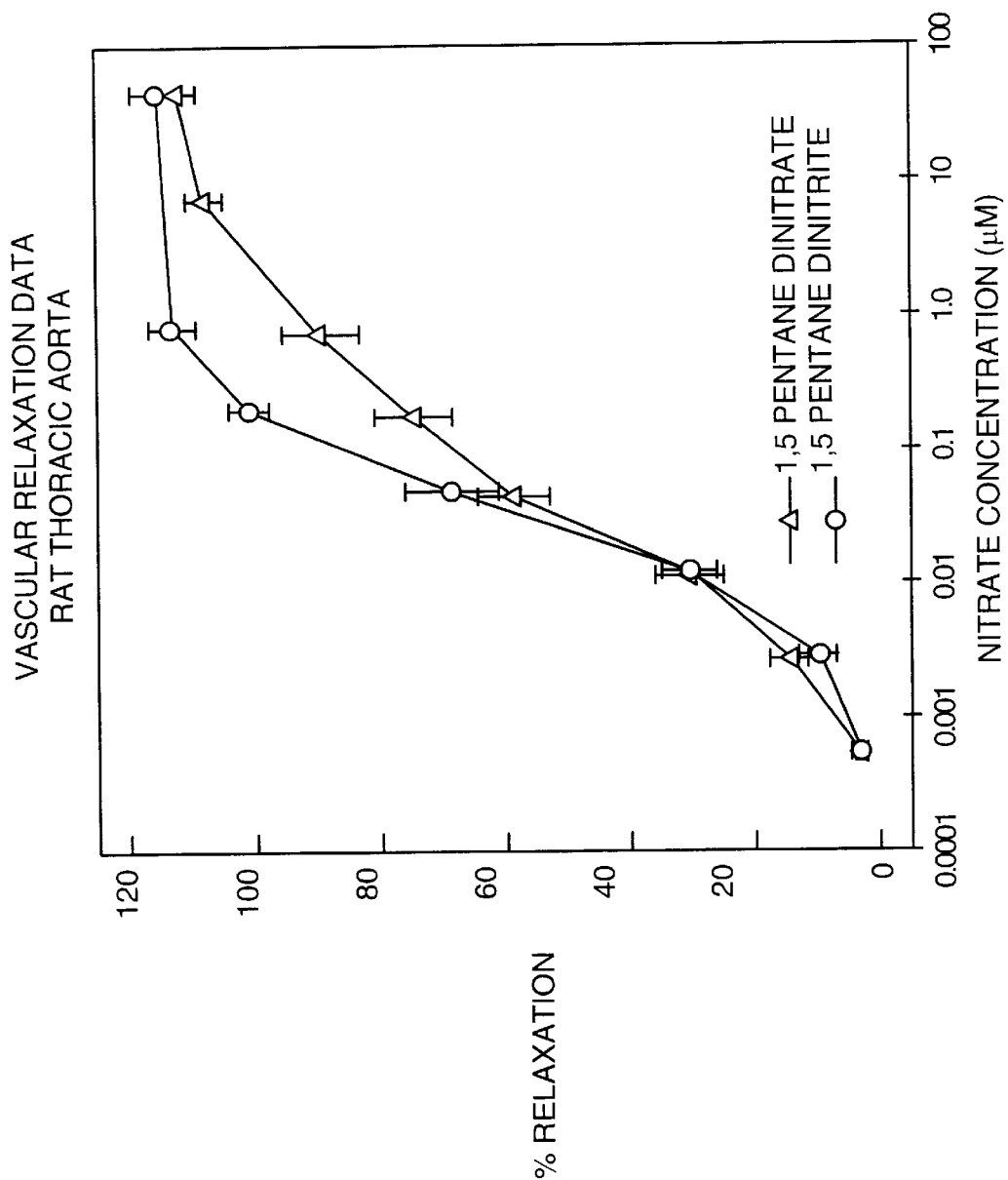
FIG. 10 is a graph comparing the vascular relaxing effects of 1,5-PDN and 1,5-pentane dinitrite at varying molar concentrations as determined by tension reductions in rat aortic rings precontracted with phenylephrine.

Aortic rings (2–3 mm wide) from Sprague-Dawley rats were isolated and placed in a tissue bath. The vessels were precontracted with small amounts of phenylephrine. A transducer connected to a recorder was used to assess changes in tension. As noted in FIG. 10, there was no difference in vascular relaxation, either in potency or efficacy, between 1,5-PDN and 1,5-pentane dinitrite.

Figure 11:
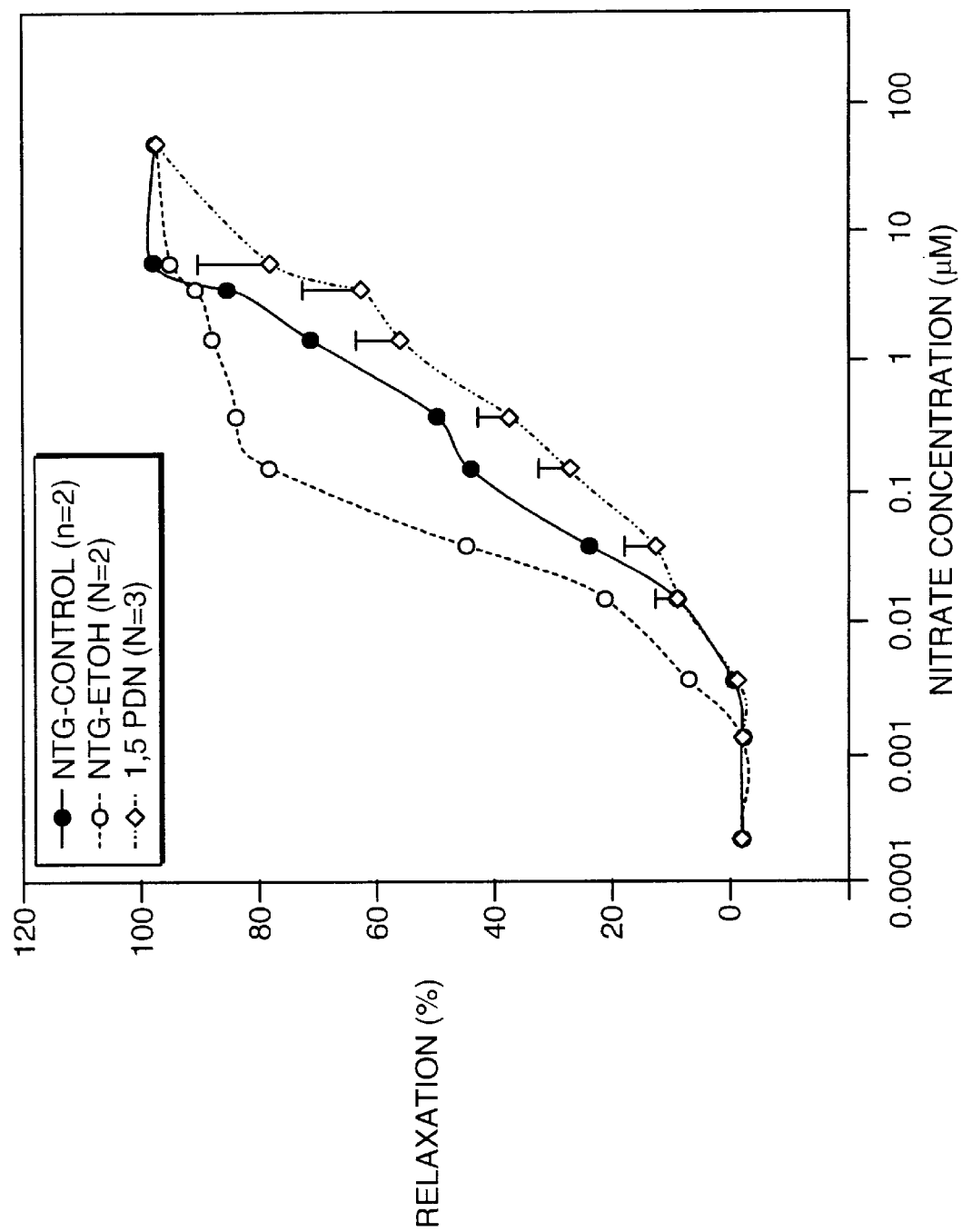
FIG. 11 is a graph comparing the vascular relaxing effect of 1,5-PDN and NTG at varying molar concentrations as determined by tension reductions in rat aortic strips precontracted with phenylephrine.

In a similar experiment, there was no appreciable difference in the vascular relaxation induced by NTG and 1,5-PDN (FIG. 11).

EXAMPLE 8

Human Experience

Two 5% formulations of 1,5-PDN in petrolatum and KY-JELLY®, respectively, were tested one week apart in one male human subject. In the privacy of his home, he noted that the petrolatum formulation provided a full erection within several minutes after topical application of about 10–20 mg of drug to his penis. The KY-JELLY® formulation resulted in less dramatic erection in about the same amount of time. No headache was associated with either drug application, indicating that little downstream systemic vasodilation was occurring.

The following studies were performed to define the pharmacokinetic parameters of 1,5-PDN and its metabolites in rats, including blood levels after dosing by various routes and metabolic fate.

EXAMPLE 9

Test Procedure

Ten male rats were fasted for 16–18 hours then dosed with 5 mg/kg of $^{14}$C-1,5-PDN orally (in corn oil) or subcutaneously (in PEG 400). Blood samples were collected via the tail vein and pooled at predetermined times up to 24 hours post-dose. An aliquot of each pooled sample was removed and analyzed for total radio activity, the remainder was extracted with acetonitrile and analyzed by HPLC to quantitate 1,5-PDN and metabolites.

Results

Figure 12:
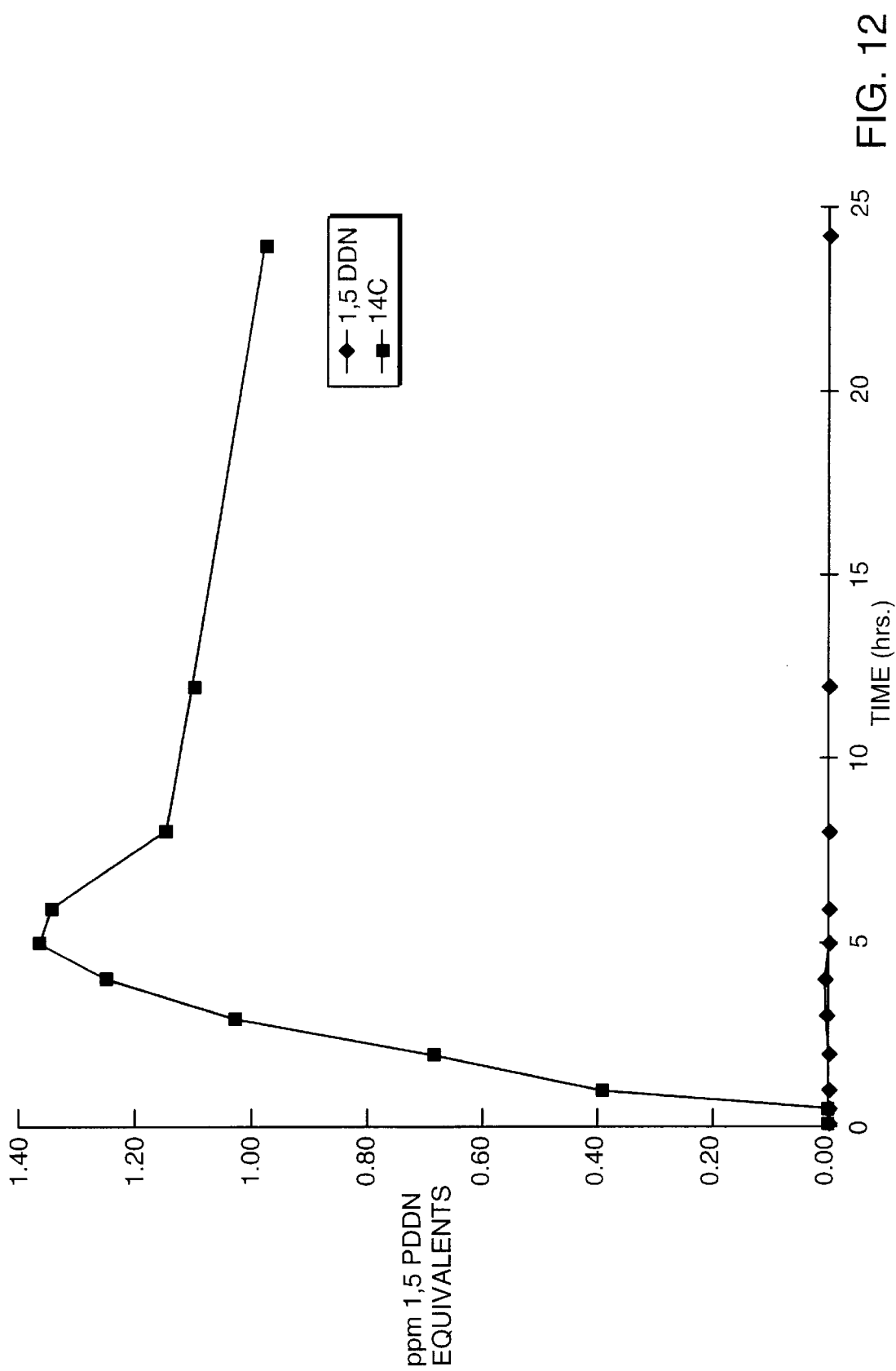
FIG. 12 is a graph comparing the blood levels of total radioactivity and 1–5 PDN following a single oral dose (5.2 mg/kg) of $^{14}$C-1,5 PDN.
Figure 13:
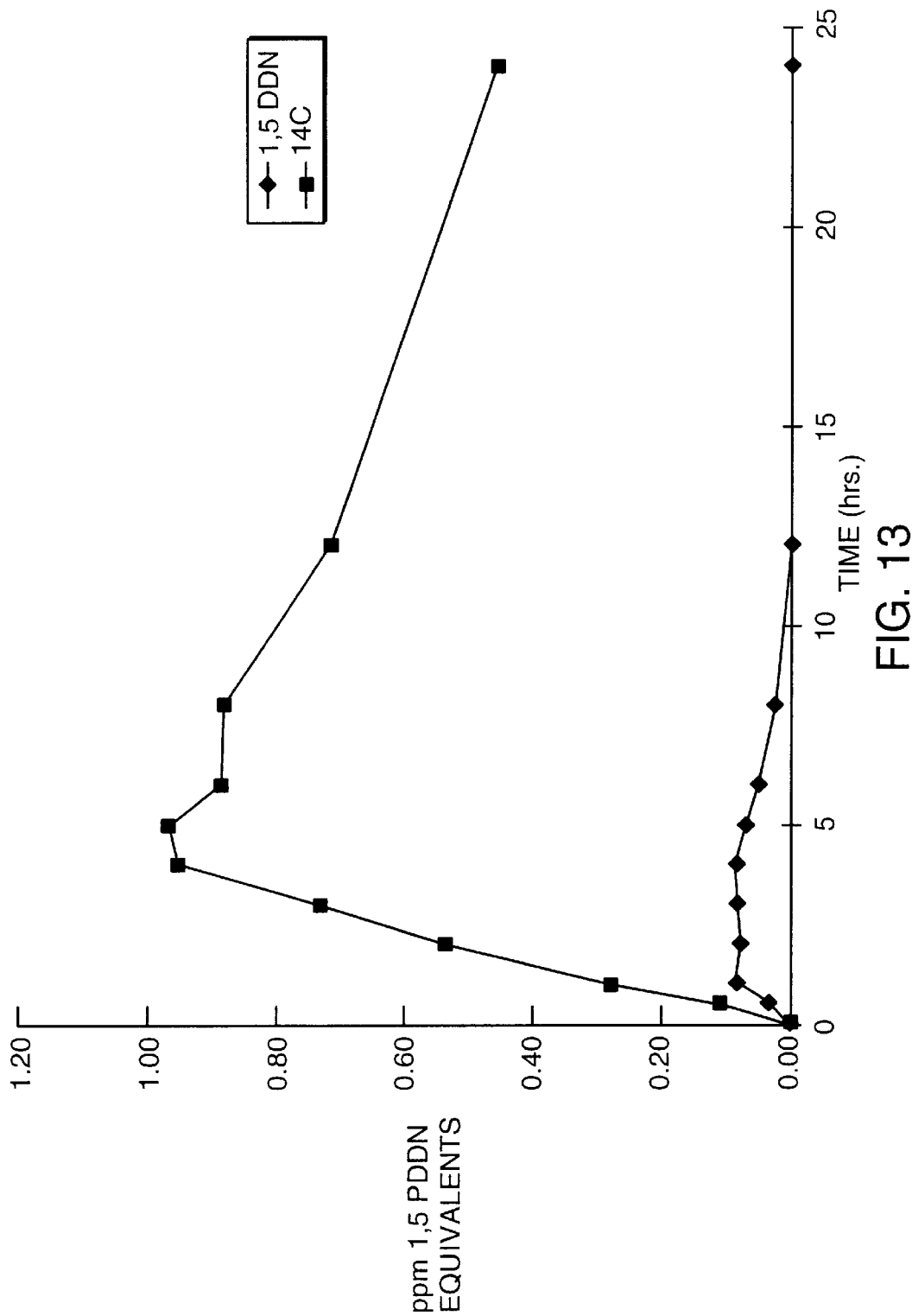
FIG. 13 is a graph comparing the blood levels of total radioactivity and 1–5 pdn following a single subcutaneous dose (5.0 mg/kg) of $^{14}$C-1,5 PDN.

The blood kinetic data for total radioactivity and 1,5-PDN are shown graphically in FIGS. 12 and 13 for oral and subcutaneous dosing, respectively. The data shows that levels of 1,5-PDN in the blood are less than 0.1% of the total radioactivity levels following oral dosing and 3.4% of the total radioactivity levels following subcutaneous dosing. These data indicate that 1,5-PDN is very rapidly metabolized in vivo and that systemic exposure to the compound is minimal. The lack of significant systemic exposure indicates that the effects of 1,5-PDN are likely to be local, rather than systemic.

EXAMPLE 10

Test Procedure

Ten rats (five male and five female) were fasted for 16–17 hours prior to IV, oral, or dermal administration of 5 mg/kg of $^{14}$C-1,5-PDN. The rats were placed in Roth metabolism cages to allow separate collection of urine, feces and $^{14}$C volatiles trapped in ethanolamine/2-ethoxyethanol at predetermined intervals up to 168 hours post-dose. At 168 hours post-dose the animals were euthanized by exsanguination following heart puncture and selected tissues were removed. The blood, plasma, harvested tissues and residual carcasses were analyzed for total radioactivity.

Results:

The principal route of elimination of IV, oral or dermal dosed radioactivity for both males and females was via the expired air as $^{14}CO_2$ (identified by barium precipitation). The animals eliminated approximately 60% of the dosed radioactivity as $^{14}CO_2$, 30% in the urine and 5% in the feces. Tissue levels of radioactivity ranged from 0.1–1 ppm and accounted for approximately 5% of dose. The treated skin for the dermal dose group contained only 1–2% of dose. This data demonstrates the compound is well absorbed through both oral and dermal routes, and is rapidly and extensively metabolized in vivo, largely to $CO_2$. Elimination of radioactivity is principally via expiration as $^{14}CO_2$. The compound appears to be handled in a similar manner by both males and females.

It has thus been shown that there are provided compositions and methods which achieve the various objects of the invention and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed as new and desired to be protected by Letters Patent is set forth in the following claims:

1. A pharmaceutical composition for the treatment of male impotence or erectile dysfunction comprising an organic mono- or dinitrate in a pharmaceutically acceptable topical or parenteral carrier, said mono- or dinitrate being selected from the group consisting of 1,5-pentane dinitrate, 1,4-butane dinitrate, 1,6-hexane dinitrate, 1,7-heptane dinitrate, isoamyl nitrate, isobutyl nitrate, neopentyl nitrate, cyclopentyl nitrate, 2-pentane nitrate, 1-pentene-5-nitrate, and 2-methyl-2-butene-4-nitrate, wherein said organo mono- or dinitrate is present in an amount effective to treat impotence or erectile disfunction.

2. A composition according to claim 1 wherein said carrier is a topical carrier.

3. A composition according to claim 2 wherein said topical carrier is selected from the group consisting of ointments, gels, creams, lotions, liquids, sprays, patches and tapes.

4. A composition according to claim 2 wherein said topical carrier is an ointment.

5. A composition according to claim 2 which comprises sufficient organic mono- or dinitrate to provide about 0.1 mg–40 mg of nitrate per dose applied to the penis.

6. A composition according to claim 5 which comprises about 15 mg of mono-or dinitrate per dose.

7. A composition according to claim 5 wherein said dose comprises about 50–800 mg of topical composition.

8. A composition according to claim 1 wherein said carrier is a parenteral carrier.

9. A composition according to claim 8 wherein said carrier includes a non-aqueous solvent or diluent.

10. A composition according to claim 9 wherein said solvent or diluent is ethanol, benzyl alcohol or propylene glycol.

11. A composition according to claim 8 which contains sufficient mono- or dinitrate to provide about 0.01–1.0 mg of dinitrate per dose injected into the penis.

12. A composition according to claim 11 wherein said dose comprises about 0.1–0.5 ml of parenteral composition.

13. A composition according to claim 1 comprising 1,5-pentane dinitrate.

14. A method of treating male impotence or erectile dysfunction in humans by local administration to the penis of a pharmaceutical composition comprising an organic mono- or dinitrate in a pharmaceutically acceptable topical or parenteral carrier, said mono- or dinitrate being selected from the group consisting of 1,5-pentane dinitrate, 1,4-butane dinitrate, 1,6-hexane dinitrate, 1,7-heptane dinitrate, isoamyl nitrate, isobutyl nitrate, neopentyl nitrate, cyclopentyl nitrate, 2-pentane nitrate, 1-pentene-5-nitrate, and 2-methyl-2-butene-4-nitrate, wherein said organo mono- or dinitrate is present in an amount effective to treat impotence or erectile disfunction.

15. A method according to claim 14 wherein said composition is administered by topical application or intracavernosal injection.

16. A method according to claim 15 wherein said composition is applied topically to the penis.

17. A method according to claim 16 wherein said carrier is a topical carrier.

18. A method according to claim 17 wherein said topical carrier is selected from the group consisting of ointments, gels, creams, lotions, liquids, sprays, patches and tapes.

19. A method according to claim 16 wherein said topical carrier is an ointment.

20. A method according to claim 16 wherein said composition contains sufficient organic mono- or dinitrate to provide about 0.1–40 mg of dinitrate per dose applied to the penis.

21. A method according to claim 20 wherein said composition comprises about 15 mg of mono- or dinitrate per dose.

22. A method according to claim 20 wherein said dose comprises about 50–800 mg of topical composition.

23. A method according to claim 14 wherein said composition is injected intracavernosally.

24. A method according to claim 23 wherein said carrier is a parenteral carrier.

25. A method according to claim 24 wherein said carrier is a non-aqueous solvent or diluent.

26. A method according to claim 25 wherein said solvent or diluent is ethanol or propylene glycol.

27. A method according to claim 23 wherein said composition comprises sufficient organic mono- or dinitrate to provide about 0.01–1.0 mg of nitrate per injectable dose.

28. A method according to claim 27 wherein said composition comprises about 0.1–0.5 ml of parenteral composition.

29. A method according to claim 14 wherein said composition comprises 1,5-pentane dinitrate.

* * * * *